(12) United States Patent
Docherty et al.

(10) Patent No.: US 7,094,809 B2
(45) Date of Patent: Aug. 22, 2006

(54) **METHOD OF TREATING SUBJECT INFECTED WITH *NEISSERIA GONORRHEA***

(75) Inventors: John Docherty, Kent, OH (US); Chun-che Tsai, Kent, OH (US)

(73) Assignees: Northeastern Ohio Universities College of Medicine, Rootstown, OH (US); Kent State University, Kent, OH (US)

( * ) Notice: Subject to any disclaimer, the term of this patent is extended or adjusted under 35 U.S.C. 154(b) by 424 days.

(21) Appl. No.: 10/459,101

(22) Filed: Jun. 11, 2003

(65) Prior Publication Data

US 2003/0203974 A1 Oct. 30, 2003

Related U.S. Application Data

(62) Division of application No. 09/930,513, filed on Aug. 15, 2001, now Pat. No. 6,599,945.

(60) Provisional application No. 60/225,609, filed on Aug. 15, 2000.

(51) Int. Cl.
*A61K 31/05* (2006.01)
*A61K 31/065* (2006.01)

(52) U.S. Cl. ................... 514/733; 514/731; 514/734
(58) Field of Classification Search ............... 514/733, 514/734, 731
See application file for complete search history.

(56) References Cited

U.S. PATENT DOCUMENTS

| | | | |
|---|---|---|---|
| 3,928,399 A | 12/1975 | Couttet et al. | |
| 4,001,137 A | 1/1977 | Steinstrasser | |
| 4,153,509 A | 5/1979 | Schwartz | |
| 5,420,361 A | 5/1995 | Grund | |
| 5,470,728 A | 11/1995 | Grund | |
| 6,197,834 B1 | 3/2001 | Docherty | |
| 6,355,692 B1 | 3/2002 | Docherty | |
| 6,599,945 B1 | 7/2003 | Docherty et al. | |

FOREIGN PATENT DOCUMENTS

DE 280030 8/1990

OTHER PUBLICATIONS

"Antibiotic Disk Suceptiblity Tests with *Neisseria Gonorrhea*", Maier et al., Antimicrobial Agents and Chemotherapy, Mar. 1974, p. 210-216.*
"Resveretrol inhibition of herpes simplex virus replication" by Docherty, et al., Antiviral Research, 43 (1999) pp. 145-155.
"Resveretrol selectively inhibits *Neisseria gonorrheae* and *Neisseria meningitidis*" by Docherty, et al., Journal of Antimicrobial Chemotherapy, 47:243-244, Feb. 2001.
"Resveretrol inhibits the growth of *Helicobacter pylori in Vitro*" by Mahady, et al, American Journal of Gastroenterology, 95:1849, Jul. 2000.
"Antibacterial Constituents of *Ficus barteri* Fruits" by Ogungbamila, et al., International Journal of Pharmacognosy, vol. 35, No. 3, 1997, pp. 185-189.
Abstract 767 "Inhibition of HSV-1 Replication by Polyphenol Analogs" by Lesniewski, et al., 40th Interscience Conference on Antimicrobial Agents and Chemotherapy, Toronto, Ontario, Canada, Sep. 17-20, 2000.
Abstract 86 "Hydroxytolan Analog Inhibition of HSV-1 Replication" by Lesniewski, et al., Fourteenth International Conference on Antiviral Research, Seattle, Washington, Apr. 8-12, 2001.
"In Vivo and In Vitro Antiherptic Effects of Polyphenols" by Lesniewski, et al., 41st Interscience Conference on Antimicrobial Agents and Chemotherapy, Chicago, Illinois, Dec. 16-19, 2001.

* cited by examiner

*Primary Examiner*—Brian-Yong S. Kwon
(74) *Attorney, Agent, or Firm*—Calfee, Halter & Griswold LLP

(57) ABSTRACT

The present invention provides a method of inhibiting the formation of infectious herpes virus particles, particularly infectious herpes simplex virus (HSV) particles, in a host cell. The method involves administering an effective amount of a hydroxylated tolan, particularly a polyhydroxylated tolan, to a herpes virus infected host cell. The present invention also provides a method of treating a herpes virus infection, particularly an HSV infection. The method comprises administering a topical composition comprising a therapeutically effective amount of a hydroxylated tolan to a herpes virus-infected site. The present invention also relates to a topical composition for treating a herpes virus infection selected from the group consisting of an HSV infection, a cytomegalovirus infection, and a varicella zoster virus infection. The present invention also provides a method of treating a subject infected with *Neisseria gonorrhea*.

3 Claims, 12 Drawing Sheets

Hydroxytolans

Synthesis of Polyhydroxytolans

1: 4,4'-(OH)$_2$
2: 3,4'5-(OH)$_3$
3: 3,3',5,5'-(OH)$_4$

INHIBITION OF HSV IN VITRO BY TOLAN-5

Tolan-5's Effect on ICP-4 Synthesis

- Vero cells infected with HSV-1 were treated with Tolan-5 for 24 hours and without for 24 hours (control).

- Lane 1 : treated w/ 105 µM Tolan-5
- Lane 2 : treated w/ 79.25 µM Tolan-5
- Lane 3 : treated w/ 52.5 µM Tolan-5
- Lane 4 : untreated cells

Tolan-5's Effect on ICP-27 Synthesis

- Vero cells infected with HSV-1 were treated with Tolan-5 for 24 hours and without for 24 hours (control).

- Lane 1 : untreated cells
- Lane 2 : treated w/ 52.5 µM Tolan-5
- Lane 3 : treated w/ 79.25 µM Tolan-5
- Lane 4 : treated w/ 105 µM Tolan-5

METHOD OF TREATING SUBJECT INFECTED WITH *NEISSERIA GONORRHEA*

This application is a divisional of U.S. application Ser. No. 09/930,513, filed Aug. 15, 2001, patented U.S. Pat. No. 6,599,945, which claims priority to U.S. Provisional Application No. 60/225,609, filed Aug. 15, 2000.

BACKGROUND

The present invention relates to compositions which inhibit replication of herpes virus and the bacterium *Neisseria gonorrheae*, and methods of using such compositions to treat subjects infected with these microorganisms.

Human herpes viruses can infect host cells in virtually any organ of the human body. Replication of a herpes virus within an infected host cell leads to lysis of the infected cell and the release of large numbers of infectious virus. The infectious particles released from the lysed cell can infect and destroy other cells at or near the site of the initial infection. These infectious particles can also be transmitted to a non-infected individual. Human herpes viruses can also enter and remain latent, i.e., in the non-replicative state, in other cells of the afflicted individual for life. This life-long infection serves as a reservoir of infectious virus for recurrent infections in the afflicted individual and as a source of infection for an unwitting contact.

At least four of the human herpes viruses, including herpes simplex virus type 1 (HSV-1), herpes simplex virus type 2 (HSV-2), cytomegalovirus (CMV), and varicella zoster virus (VZV) are known to infect and cause lesions in the eye of certain infected individuals. Together, these four viruses are the leading cause of infectious blindness in the developed world.

HSV-1 primarily infects the oral cavity, while HSV-2 primarily infects genital sites. However, any area of the body, including the eye, skin and brain, can be infected with either type of HSV. Generally, HSV is transmitted to a non-infected individual by direct contact with the infected site of the infected individual.

The initial symptoms of a primary or recurrent HSV infection include tingling, pain, and/or parasthesia at the site of infection. This is followed by formation of a lesion at the infected site, i.e., in the oral cavity, eye, skin, or reproductive tract. Healing typically occurs in approximately ten to fourteen days.

The immune reaction that occurs in response to an HSV infection prevents dissemination of the virus throughout the body of the immunocompetent individual. Such immune reaction, however, does not eliminate all infectious HSV particles from the body of the afflicted individual. The virus particles that are not killed by the immune response move along the nerve path to the ganglia of the infected individual where they remain in a state of latency. In response to a variety of stimuli including stress, environmental factors, other medications, food additives or food substances, the infectious virus particles may leave the ganglia and cause a recurrent infection at or near the original site of infection. In those HSV-infected individuals who are immunosuppressed or who lack a well-developed immune system, such as neonates, dissemination of the virus particles from the infected site can also occur and lead to life-threatening complications, including encephalitis.

VZV, which is transmitted by the respiratory route, is the cause of chickenpox, a disease which is characterized by a maculopapular rash on the skin of the infected individual. As the clinical infection resolves, the virus enters a state of latency in the ganglia, only to reoccur in some individuals as herpes zoster or "shingles". The reoccurring skin lesions remain closely associated with the dermatome, causing intense pain and itching in the afflicted individual.

CMV is more ubiquitous and may be transmitted in bodily fluids. The exact site of latency of CMV has not been precisely identified, but is thought to be leukocytes of the infected host. Although CMV does not cause vesicular lesions, it does cause a rash.

There are no known cures for infections with human herpes viruses, i.e., methods of eliminating the virus from the body of the infected individual. In addition, there are very few methods for blocking the formation of infectious herpes virus particles and thereby reducing the frequency, severity, or duration of a herpes virus-induced infection and the likelihood of recurrence of infection in the latently-infected individual. Thus, it is desirable to have additional methods for inhibiting the formation of infectious herpes virus particles. Such method is useful for limiting the severity of a herpes virus infection within an infected individual and the likelihood of transmission of the herpes virus infection from the infected individual to a non-infected individual.

*Neisseria gonorrhea* is a gram negative bacterium that is pathogenic in humans. The bacterium is spread from person to person by contact with infected secretions, most often by sexual contact. Once the pathogen is deposited on a mucosal surface, a complex series of molecular interactions occur that result in invasion of mucosal columnar cells. The spectrum of diseases ranges from local infections of the urethral, cervical, rectal and oropharyngeal membranes to invasion of the pelvis or epididymis, to invasion of the blood stream, with or without dissemination to distant organs such as heart valves, joints, and pericardium. The pathogen may also infect the conjunctiva. Gonococcal conjunctivitis is most often contracted by neonates passing through an infected birth canal, although adults can also be infected.

The quest for a gonococcal vaccine has been ongoing for many years with virtually no success. Accordingly, the primary treatment involves preexposure or postexposure antibiotic prophylaxis. In addition to antibiotic eyedrops, silver nitrate has also been used to treat neonatal gonococcal conjunctivitis. Unfortunately, the bacterium has developed resistance to some of the most common antibiotics, such as penicillin. Accordingly, additional compositions for reducing growth of this pathogen are desirable.

SUMMARY OF THE INVENTION

The present invention provides a new method of inhibiting the formation of infectious herpes virus particles, particularly infectious HSV particles, in a host cell. The method involves administering a hydroxylated tolan, particularly dihydroxytolan or trihydroxytolan, to a herpes virus infected host cell. The hydroxylated tolan is administered to the host cell in an amount sufficient to inhibit replication of the virus in the virus-infected host cell. Such method is useful for reducing the cytopathic effect of a herpes virus infection. Such method is also useful for preventing the spread of the herpes virus from a virus-infected host cell to a non-infected host cell. Such method is also useful for establishing a model system for studying the molecular events that occur during replication of herpes virus and for studying the factors that trigger replication of a latent herpes virus, particularly replication of latent HSV.

The present invention also provides a method of treating a subject having or suspected of having a herpes virus infection, particularly an HSV infection. The method comprises administering a topical composition comprising a therapeutically effective amount of a hydroxylated tolan, particularly a di-hydroxylated or tri-hydroxylated tolan, to a herpes virus-infected site. The present invention also relates to a topical composition for treating a herpes virus infection selected from the group consisting of an HSV infection, a CMV infection, and a VZV infection.

The present invention also provides a method of inhibiting replication of the gram negative bacterium *Neisseria gonorrhea*. Such method involves contacting the bacterium with a composition containing a hydroxylated tolan, preferably a di-hydroxylated or tri-hydroxylated tolan. In vivo, such method can be used to treat an individual who has come in contact with, (e.g., a carrier), or an individual who is expected to come into contact with the bacterium. In vivo, such method comprises administering a composition comprising a therapeutically effective amount of a hydroxylated tolan, particularly a tri-hydroxylated tolan to the subject

DETAILED DESCRIPTION OF THE INVENTION

Figure 1:
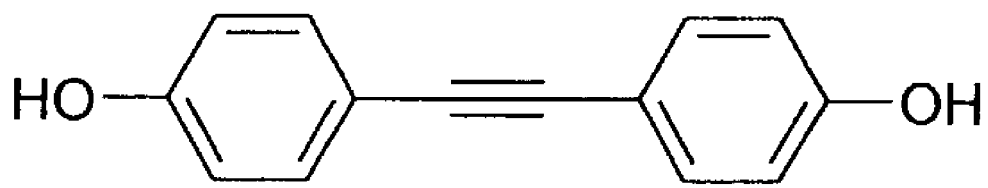
FIG. 1 shows the structures of 4,4' dihydroxytolan ("Tolan-5"), 3,4',5-trihydroxytolan ("Tolan-10") and 4-hydroxy-4'-trifluoromethyltolan ("Tolan-11").
Figure 1:
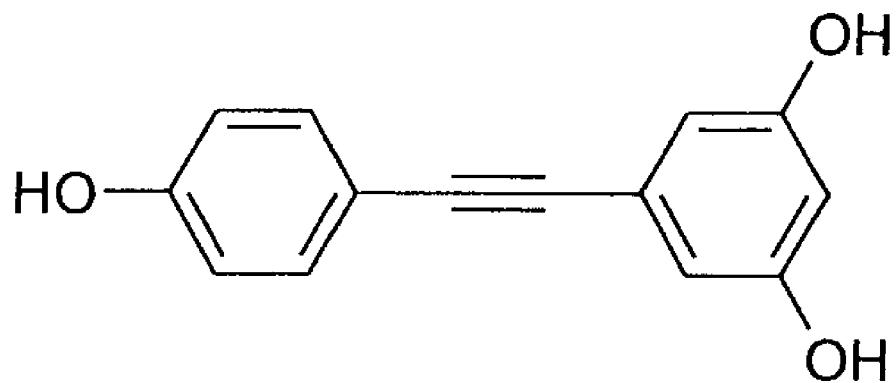
Figure 1:

In one aspect, the present invention provides a method of inhibiting formation of infectious herpes virus particles, particularly infectious HSV particles, in a host cell. The method comprises a hydroxylated tolan to the host cell. The hydoxylated tolan is administered in an amount sufficient to or effective to inhibit replication of the herpes virus within the infected cell. Preferably, the hydroxylated tolan, is administered to the host cell either prior to infection of the host cell with the virus or within six hours after infection of the host cell with the virus.

Preferably, the hydroxylated tolan is administered to the host cell by contacting the host cell with or exposing the host cell to a composition comprising the hydroxylated tolan. For example, in vitro, the method comprises adding a hydroxylated tolan to the culture medium of herpes virus-infected host cells. In the case of cultured cells, the hydroxylated tolan preferably is added to the medium before the host cells are infected with the virus or within six hours after the host cells are infected with the virus. In the case of ganglia, which serves as an organ culture model system for studying latency of herpes viruses, particularly for studying latency of HSV, the hydroxylated tolan is added to the medium after the ganglia are excised from the latently-infected host.

It has been determined that treatment of cultured cells in accordance with the present method is non-toxic to cells and blocks replication of HSV at some early stage in the replicative cycle of this human herpes virus. It has also been determined that the effect of a polyhydroxylated tolan on HSV replication is reversible. Typical of the herpes viruses, HSV replication occurs in phases, with each phase being dependent on the successful completion of the prior phase. The "immediate early phase" occurs at 1–3 hours after infection and is associated with regulatory and synthetic events. The "early phase" occurs 3–6 hours after infection and is also associated with regulatory and synthetic events, particularly the synthesis of virus DNA. The "late phase" occurs 6–10 hours after infection and is associated with final synthetic events and assembly of viral components into infections virions. Accordingly, since all herpes viruses have in common a replicative scheme that progresses through similar and distinct phases, such method is useful for establishing model systems for studying the molecular events that occur during replication of all herpes viruses. For example, mammalian cell cultures incubated in the presence and absence of a hydroxylated tolan may be used to identify cellular factors that are involved in regulating herpes virus synthetic events. Such cell cultures may also be employed to characterize the role of HSV gene products in the replication of infectious virus, particularly those proteins and factors whose function are currently unknown.

Such method is also useful for establishing a model system for studying latency of herpes viruses, particularly latency of the herpes viruses that remain latent in the ganglia, such as for example HSV and VZV. Such model system is useful for characterizing the extracellular factors such as for example hormones and cytokines, as well as the intracellular factors and molecular events that trigger replication of latent herpes viruses.

Methods and Compositions for Treating a Subject with a Herpesvirus Infection

In another aspect, the present invention provides methods for treating a subject with a herpesvirus infection. The method comprises administering a pharmaceutical composition, preferably a topical composition, comprising a therapeutically effective amount of a hydroxylated tolan, preferably a dihydroxylated tolan or trihydroxylated tolan, to the site of the infection. As used herein "site of the infection" means a previously uninfected site which is expected to come into contact with a herpes virus-infected site or the site of a current or prior herpes virus-induced lesion. Such method is particularly useful for treating local herpes virus infections, such as for example, HSV-induced skin lesions, HSV-induced eye infections, HSV-induced lesions of the reproductive tract, CMV-induced eye lesions, and VZV-induced eye lesions. In such cases, it is preferred that the hydroxylated tolan be applied directly to the infected site. It is preferred that the hydroxylated tolan be administered to the herpesvirus-infected site in the form of an aqueous solution or in the form of a salve. For eye infections, it is preferred that an aqueous solution of the hydroxylated tolan, be administered as an eye drop. For herpesvirus skin lesions, such as for example, HSV-induced skin lesions, or HSV-induced lesions of the reproductive tract, it is preferred that the composition be applied topically.

Method of Inhibiting Growth of *Neisseria gonorrheae*

In another aspect, the present invention provides a method of inhibiting the growth of *Neisseria gonnorhea*. The method comprises administering a hydroxylated tolan, preferably a dihydroxlated or trihydroxylated tolan to a surface which has come in contact with or could come in contact with the organism. In vivo, the method, which comprises administering the hydroxylated tolan to a mucous membrane of a human subject, may be used to prevent or reduce the symptoms of gonococcal disease in the human subject. The hydroxylated tolan may be incorporated into a pharmaceutical composition which is applied to the mucous membrane of a carrier of the bacterium or a person who could come into contact with the carrier.

Administration of the pharmaceutical composition to an uninfected subject is via local administration to a site which has been or may be contacted with the pathogenic organism. It is preferred that the pharmaceutical composition be applied prior to exposure to the targeted pathogen or preferably within 1–24 hours, more preferably within 1–12 hours after exposure of the uninfected subject to the pathogenic organism. Administration of the pharmaceutical composition to a carrier of *Neisseria gonorrhea* is via local administration to the genitalia, rectum, or oropharynx.

Hydroxylated Tolans

Figure 2:
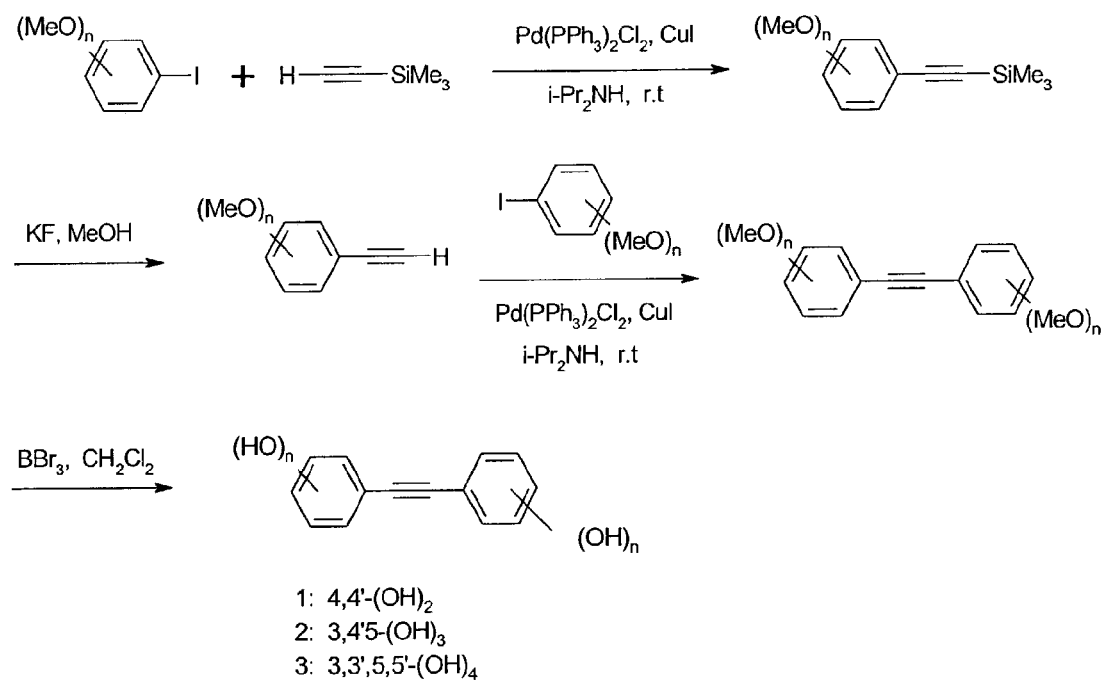
FIG. 2 is a synthetic scheme for making hydroxylated tolans.
Figure 3:
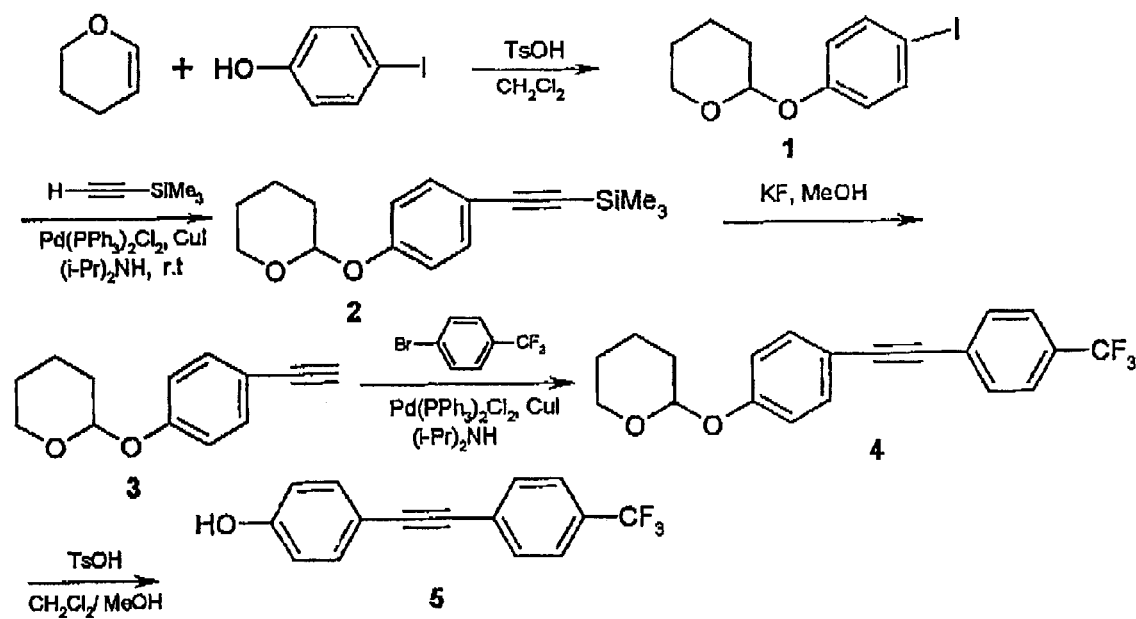
FIG. 3 is a synthetic scheme for making hydroxylated trifluoromethyltolans.

The structural skeleton of the compound employed in the present invention, i.e., the hydroxylated tolan, comprises two aromatic rings joined by an acetylene bridge. Preferably, the hydroxylated tolan is a polyhydroxylated tolan, more preferably a dihydroxytolan, or a trihydroxytolan, most preferably a trihydroxytolan. A general scheme for preparing polyhydroxylated tolans is shown in FIG. 2. A general scheme for preparing a hydroxylated trifluormethyltolan is shown in FIG. 3.

Topical Composition

The pharmaceutical composition comprises a therapeutically effective amount of a hydroxylated tolan, preferably a polyhydroxylated tolan, more preferably a dihydroxylated or trihyroxylated tolan, and a pharmaceutically acceptable carrier, preferably a topical carrier. Preferably, the composition comprises a relatively inert topical carrier. Many such carriers are routinely used and can be identified by reference to pharmaceutical texts. Examples include polyethylene glycols, polypropylene copolymers, and some water soluble gels. Such a composition, referred to hereinafter as the "topical composition", may also contain diluents, fillers, salts, buffers, stabilizers, solubilizers, and other pharmaceutically acceptable materials well known in the art. The term "pharmaceutically acceptable" means a non-toxic material that does not interfere with the effectiveness of the antiviral or antibacterial activity of the hydroxylated tolan.

In practicing the present method of treatment or use, a pharmaceutical composition comprising a therapeutically effective amount of the hydroxylated tolan is applied to the site of infection in the host subject before or after the host subject is exposed to the virus or bacterium. Such composition is particularly effective in treating infections of the eye, oral cavity and vagina as well as border areas of the lips and rectum. In the case of oral administration, dentrifices, mouthwashes, tooth paste or gels, or mouth sprays are used. Vaginal or rectal administration may be by the usual carriers such as douches, foams, creams, ointments, jellies, and suppositories, the longer lasting forms being preferred. Ocular administration is preferably by ophthalmic ointments or solutions. Lip treatment is, preferably, in the form of a gel.

The topical composition may further contain other agents which either enhance the activity of the hydroxylated tolan or complement its activity or use in treating the viral disease or bacterial disease. Such additional factors and/or agents may be included in the pharmaceutical composition to produce a synergistic effect with the hydroxylated tolan, or to minimize side effects. The topical composition may also contain an agent which enhances uptake of the hydroxylated tolan.

Preferably the topical composition comprises a solvent for the hydroxylated tolan, such as, for example, an alcohol. A liquid carrier such as water, petroleum, oils of animal or plant origin such as peanut oil, mineral oil, soybean oil, or sesame oil, corn oil, or synthetic oils may be added. The liquid form of the pharmaceutical composition may further contain a physiological saline solution, dextrose or other saccharide solution, or glycols such as ethylene glycol, propylene glycol or polyethylene glycol. The preparation of such topical composition having suitable pH, isotonicity, and stability, is within the skill in the art.

The topical composition of the invention may be in the form of a liposome in which the hydroxylated tolan is combined with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art.

Dosage

The hydroxylated tolan is administered to the site of infection in the host subject in a therapeutically effective amount. As used herein, the term "therapeutically effective amount" means the total amount of the hydroxylated tolan that is sufficient to show a meaningful benefit, i.e., treatment, healing, prevention, amelioration, or reduction in the symptoms of the herpesvirus or gonococcal infection or an increase in rate of healing, amelioration or reduction in the symptoms of such infection.

By "treating" is meant curing or ameliorating a herpesvirus or gonococcal infection or tempering the severity of the infection. By preventing is meant blocking the formation of a primary lesion or recurrence of a lesion at the infected site. The dosages of the hydroxylated tolan, which can treat or prevent an HSV, VZV, CMV infection, or gonococcal infection, can be determined in view of this disclosure by one of ordinary skill in the art by running routine trials with appropriate controls. Comparison of the appropriate treatment groups to the controls will indicate whether a particular dosage is effective in preventing or treating the infection at the levels used in a controlled challenge.

It is contemplated that the various pharmaceutical compositions used to practice the method of the present invention should contain about 0 μg to about 100 mg/ml. Although a single application of the topical composition may be sufficient to ameliorate the pathological effects of the herpesvirus or *Nisseria gonorrhea*, it is expected that multiple doses will be preferred.

Delivery

Administration of the pharmaceutical composition is via local administration to the infected site. In those individuals who have experienced a primary lesion, it is preferred that the topical composition be applied at the prodromal stage of infection, i.e., during early symptoms of pain, tingling, parasthesia. Preferably, the composition is applied to the site of infection periodically, more preferably every three hours. The duration of therapy using the pharmaceutical composition of the present invention will vary, depending on the severity of the disease being treated and the condition and response of each individual patient. Ultimately the attending physician will decide on the appropriate duration of using the pharmaceutical composition of the present invention.

The following examples are for purposes of illustration only and are not intended to limit the scope of the claims which are appended hereto. All references cited herein are specifically incorporated in their entirety herein.

EXAMPLE 1

Synthesis of Poly-Hydroxylated Tolans

A. Synthesis of 3,5-dimethoxyiodobenzene from 3,5-dimethoxyaniline

In a 500 ml 3-necked, round-bottomed flask equipped with a thermometer, a mechanical stirrer and an addition funnel was placed HCl (12 M, 100 ml, 1.2 mol) and crushed ice (100 g). The flask was immersed in a dry ice-Me$_2$CO cooling bath, and 3,5-dimethoxyaniline (15.3 g, 100 mmol) was added with stirring. To this cold mixture NaNO$_2$ (8.4 g, 120 mmol) in 40 ml H$_2$O was added dropwise at such a rate to maintain the temperature of the reaction mixture between −10~−5° C. throughout the addition. The reaction mixture was stirred for 1 hour at 0~5° C. The red dark solution of the diazonium salt was added to a well-stirred solution of KI (83 g, 500 mmol) in 200 ml H$_2$O at room temperature. The mixture was stirred for 2 hours, then allowed to stand overnight. The resulting solution was extracted with ether (200 ml×4). The pooled organic extracts were washed with brine (200 ml×2), and an aqueous saturated Na$_2$S$_2$O$_3$ solution (200 ml×2), dried over MgSO4, filtered and concentrated to a small volume. Silica gel was added, and the mixture evaporated to dryness. This preloaded silica gel was placed on a pad of silica gel and eluted with petroleum to give 17.5 g (66%) of a colorless solid, 3,5-dimethoxyiodo benzene. $^1$HNMR (CDCl$_3$, 300 Mz): δppm: 6.85 (2H, d, J=2.3, Ar—H), 6.40 (1H, t, J=2.3 Ar—H), 3.76 (s, 6H, 2CH$_3$O ).

B. Synthesis of Arylethynyltrimethylsilanes from Ethylnyltrimethylsilane and Aryl Iodides General Procedure:

To a solution of aryl methoxy substituted aryl iodide (40 mmol) in isopropylamine (250 ml) were added Pd(PPh$_3$)$_2$Cl$_2$ (0.4 mmol) and CuI (0.8 mmol), then trimethylsilylacetylene (44 mmol). The reaction mixture was stirred at ambient temperature for 2–4 hours under a slow stream of nitrogen. The reaction mixture was filtered and the residues were washed with ethyl acetate, and the solvent evaporated from the combined filtrates. The crude product was purified by column chromatography on silica gel using petroleum/ethyl acetate as an eluent to give the methoxy substituted arylethylyl trimethylsilanes.

(1) 2-(4-methoxyphenyl)-1-trimethylsilyl-ethyne

Purified by column chromatography on silica gel using petroleum ether as an eluent to give 2-(4-methoxyphenyl)-1-trimethylsilyl-ethyne (96% yield) as a light yellow oil.

(2) 2-(3,5-dimethoxyphenyl)-1-trimethylsilyl-ethyne

Purified by column chromatography on silica gel using petroleum ether as an eluent to give 2.2 g (94%) light yellow needles.

T$_{GC}$=5.39 (T$_{init}$=50° C.). $^1$HNMR(CDCl$_3$, 300 Mz) δppm: 6.6(s, 2H, Ar—H), 6.43(s, 1H, Ar—H), 3.77(s, 6H, 2CH$_3$), 0.24(s, 9H, SiMe$_3$).

C. Synthesis of Methoxy Substituted Arylacetylenes

To a solution of arylethynyltrimethylsilanes (30 mmol) in methanol (30 ml) was added potassium fluoride (3.5 g, 60 mmol). The reaction mixture was stirred at room temperature for 2 hours. After removal of methanol, the product was extracted with ether (100 ml×3) and purified by chromatography on silica gel using petroleum ether as eluent to afford pure products.

(1) p-Methoxyrthylnylbenzene

Pale yellow oil was obtained in 92% yield.

$^1$HNMR (CDCl$_3$, 300 Mz): δppm: 7.94(d, 2H, J=8.98, Ar—H), 6.83(d, 2H, J=8.55, Ar—H), 3.80(s, 3H, Ch$_3$O), 3.00 (s, 1H≡—H).

(2) 3,5-Methoxyrthylnylbenzene

Pale yellow needle was obtained in 91% yield.

$^1$HNMR (CDCl$_3$, 300 Mz): δppm: 7.94(d, 2H, J=2.4, Ar—H), 6.83(d, 2H, J=2.3, Ar—H), 3.78(s, 6H, 2Ch$_3$O), 3.94 (s, 1H≡—H).

D. Synthesis of Methoxytolans

General Procedure:

To a solution of methoxyethylnylbenzenes (20 mmol) and methoxy substituted aryl iodide (22 mmol) in isopropylamine (120 ml) were added Pd(PPH$_3$)$_2$Cl$_2$ (0.2 mmol) and CuI (0.4 mmol). The reaction mixture was stirred at ambient temperature for 6 hours under a slow stream of nitrogen. The reaction mixture was filtered and the residues were washed with ethyl acetate and the solvent evaporated from the combined filtrates. The crude product was purified by column chromatography on silica gel using petroleum ether/ethyl acetate (9:1) as an eluent to give methoxytolans.

(1) 3,4',5-Trimethoxyltolan:

A pale yellow oil was obtained in 93% yield.

$^1$HNMR (CDCl$_3$) 300 Mz): δppm: 7.46(d, 2H, J=8.6, Ar—H), 6.88(d, 2H, J=8.8, Ar—H), 6.66(d, 2H J=2.3, Ar—H), 6.44(t, 2H, J=2.3, Ar—H), 3.83(s, 3H, CH$_3$O), 3.80(s, 6H, 2CH$_3$O).

(2) 3,3',5,5'-Tetramethoxytolan:

A colorless needle crystal was obtained in 85% yield.

$^1$HNMR (CDCl$_3$) 300 Mz): δppm: 6.69(d, 4H, J=2.3, Ar—H), 6.46(d, 2H, J=2.3, Ar—H), 6.66(d, 2H, J=2.3, Ar—H), 3.80(s, 12H, 4CH$_3$O).

(3) 4,4'-Dimethoxytolan:

A colorless needle crystal was obtained in 91% yield.

$^1$HNMR (CDCl$_3$) 300 Mz): δppm: 7.46(d, 4H, J=8.7, Ar—H), 6.87(d, 2H, J=8.7, Ar—H), 3.82(s, 6H, 2CH$_3$O).

E. Synthesis of Hydroxytolans

General Procedure:

In a dry 250 ml, 3-necked, round-bottomed flask was placed a solution of methoxytolans (10 mmol) in anhydrous methylene chloride under N$_2$. The reaction mixture was cooled to below –20° C., and BBr$_3$ (20 mmol×the number of methoxy groups) by syringe. Then the reaction mixture was permitted to warm up to room temperature and stirred for over 24 hours. The reaction mixture (a reddish clear solution) was then poured into ice-water and stirred. After sufficient stirring, an aqueous NaHCO$_3$ solution was added to adjust the pH of the mixture to 7–8. Then the mixture was extracted with ethyl acetate 3–4 times. The organic layer was washed with brine and dried over MgSO$_4$. Solvent was removed under reduced pressure. The red brown color crude products was purified by column chromatography on silica gel using petroleum/ethyl acetate (1:1) as en eluent to give hydroxytolans.

(1) 3,4',5-Trihydroxytolan:

A pale yellow solid was obtained in 82% yield.

$^1$HNMR (CDCl$_3$) 300 Mz): δppm: 9.89(s, 1H, OH), 9.45(s, 2h, 2-OH), 7.33(d, 2H, J=8.65, Ar—H), 6.78(d, 2H, J=8.63, Ar—H), 6.31(d, 2H, J=2.2, Ar—H), 6.23(d, 2H, J=2.2, Ar—H).

(2) 3,3',5,5'-Tetrahydroxytolan:

A pale red solid was obtained in 92% yield.

$^1$HNMR (CDCl$_3$, 300 Mz): δppm: 9.49(s, 4H, 4-OH), 6.33(d, 4H, J=2.2, Ar—H), 6.25(t, 2H, J=2.2, Ar—H).

(3) 4,4'-Dihydroxytolan:

A white solid was obtained in 93% yield.

$^1$HNMR (CDCl$_3$, 300 Mz): δppm: 9.82(s, 2H, 2-OH), 7.31(d, 4H, J=8.7, Ar—H), 6.77(d, 4H, J=8.7, Ar—H).

References

1. Ali, M. A., Kondo, K. and Tsuda, Y., *Chem. Pharm. Bull.*, 1992, 40, 1130–1136.
2. Pavia, M. R., et. al., *Bioorg. Med. Chem.*, 1996; 4, 659–666.
3. Jeffery, T., *Tetrahedron Lett.*, 1994, 35, 3051–3054.
4. Jeffery, T. and Galland, J. C. *Tetrahedron Lett.*, 1994, 35, 4103–4106.
5. Schmidt-Radde, R. H. and Vollhardt, K. P. C., *J. Am. Chem. Soc.*, 1992, 114, 9713–9715.
6. Schumm, J. S., Pearson, D. L. and Tour, J. M., *Angew. Chem., Int. Ed. Engl.*, 1994, 33, 1360–1363.
7. Pal, M. and Kundu, N. G., *J. Chem. Soc., Perkin Trans.*, 1996, 1, 449–451.
8. Bumagin, N. A., Sukhomlinova, L. I., Luzikova, E. V., Tolstaya T. P. and Beletskaya, I. P., *Russ. J. Org. Chem.*, 1996, 32, 996–1000.
9. Bumagin, N. A., Sukhomlinova, L. I., Luzikova, E. V., Tolstaya T. P. and Beletskaya, I. P., *Tetrahedron Lett.*, 1996, 37, 897–900.
10. Meier H. and Dullweber, U., *J. Org. Chem.*, 1997, 62, 4821–4826.

EXAMPLE 2

Synthesis of 4-Hydroxy-4'-trifluoromethyltolan

FIG. 3 shows a synthetic scheme for the preparation of hydroxy-trifluoromethyltolan. Synthetic details of the specific reaction steps are described below. Most of the reactions were accomplished with high yields (over 90%). All products were purified by column chromatography and characterized by GC and $^1$HNMR spectrometry.

1. 1-Iodo-4-tetrahydropyranyloxybenzene 1.

To a stirred solution of 4-iodophenol (11.0 g, 50 mmol) in CH$_2$Cl$_2$ (50 ml) cooled with an ice bath, dihydropyran (5.0 g, 60 mmol) was added dropwise over 10 min at 0–5° C. After the solution became clear, toluenesulfonic acid, TsOH, (10 mg) was added. The solution was stirred at 20° C. for 15 min. Then it was quenched by addition of NaHCO$_3$ (1 g) and 3 drops of water, and after stirring for 5 min at 20° C., the solvent was removed in vacuo and the residue was purified by column chromatography on silica gel with petroleum ether as eluent to give 14.0 g (92%) of 1 as colorless crystal; mp 66° C.; δ$_H$(CDCl$_3$; 300 MHz): 7.55(d, J=8.3, 2H, Ar—H), 6.83(d, J=8.4, 2H, Ar—H), 5.37(t, J=3.1, 1H, OCHO), 3.86(m, 1H, THP), 3.59(m, 1H, THP), 1.87~1.58 (m, 6H, THP).

2. 4-Tetrahydropyranyloxy-1-(trimethylsilylethynyl) benzene 2.

To a degassed solution of compound 1 (9.12 g, 30 mmol) in diisopropylamine (180 ml) under nitrogen, Pd(PPh$_3$)$_2$Cl$_2$ (140 mg, 0.2 mmol) and CuI (78 mg, 0.4 mmol) were added. Then trimethylsilyl acetylene (3.3 g, 33 mmol) was added dropwise to this clear solution. The reaction mixture was stirred for 2 hours at room temperature. The salt formed during the reaction procedure was filtered off and washed well with ethyl acetate. The filtrate was evaporated to dryness and hydrolyzed with concentrated hydrochloric acid (5 ml), water (25 ml) and crushed ice (10 g), then extracted with ethyl acetate. The combined organic paste was washed with brine and dried with MgSO$_4$. The solvent was removed in vacuo and the residue was purified by column chromatography (petroleum ether-ethyl acetate=9:1) to give a yellow oil of 2. Yield 7.9 g (96%); δ$_H$(CDCl$_3$; 300 MHz): 7.39(d, J=8.7, 2H, Ar—H, 6.97(d, J=8.6, 2H, Ar—H), 5.41(t, J=3.1, 1H, OCHO), 3.84(m, 1H, THP), 3.59(m, 1H, THP), 1.86~1.61(m, 6H, THP), 0.23(s, 9H, 3 CH3).

3. 4-Tetrahydropyranyloxyphenylacetylene 3.

(9.3 g, 160 mmol) was added to a stirred solution of 2 (22.6 g, 80 mmol) in MeOH (150 ml). The reaction mixture was stirred at room temperature for about 4 hours. After the reaction finished (GC shows no starting material remaining), the solvent was removed under reduced pressure on a rotary evaporator. The residue was purified by column chromatography on silica gel (petroleum ether-ethyl acetate=9:1) to give a pale yellow crystals of 3. Yield 15.7 g(97%); mp 65° C., δ$_H$(CDCl$_3$; 300 MHz): 7.42(d, J=8.7, 2H, Ar—H), 7.00 (d, J=8.7, 2H, Ar—H), 5.43(t, J=3.2, 1H, OCHO), 3.87(m, 1H, THP, 3.60(m, 1H, THP), 2.99(s, 1H, C=C—H), 1.96~1.56(m, 6H, THP).

4. 4-Tetrahydropyranyloxy-4'-trifluormethyltolan 4.

A solution of 3 (12.1 g, 60 mmol) and 4-bromobenzotriflouride (14.85 g, 66 mmol) in diisopropylamine (250 ml) was heated to 30° C. under nitrogen, and the solution was degassed. Then Pd(PPh$_3$)$_2$Cl$_2$ (210 mg, 0.3 mmol) and copper(I) iodide (114 mg, 0.6 mmol) were added to this clear solution. The reaction mixture was stirred for 2 hours at 80°

C., then cooled to room temperature. The salt formed during the reaction procedure was filtered off and washed well with ethyl acetate. The filtrate was evaporated to dryness and hydrolyzed with concentrated hydrochloric acid (10 ml), water (100 ml) and crushed ice (50 g), then extracted with ethyl acetate. The combined organic paste was washed with brine and dried over MgSO$_4$. The solvent was removed in vacuo and the residue was purified by column chromatography (petroleum ether-ethyl acetate=9:1) to give a pale yellow crystals of 4. Yield 16.6 g (80%); mp 112~113° C.; $\delta_H$(CDCl$_3$; 300 MHz): 7.59(s, 4H, Ar—H), 7.48(d, J=8.7, 2H, Ar—H), 7.04(d, J=8.7, 2H, Ar—H), 5.46(t, J=3.1, 1H, OCHO), 3.89(m, 1H, THP), 3.62(m, 1H, THP), 1.86~1.62 (m, 6H, THP).

5. 5-Hydroxy-4'-trifluoromethyltolan 5.

Coumpound 4 (13.84 g, 40 mmol), CH$_2$Cl$_2$ (75 ml) and MeOH (125 ml) were placed in a 250 ml round bottomed flask, then TsOH (0.4 g, 0.4 mmol) was added. The reaction mixture was stirred at 30° C. for 1 hour. When the reaction was finished (TLC shows no starting material remaining), the solvent was removed by rotary evaporation and the residue was dissolved in EtOAc and filtered through silica gel. The solvent was removed and the solid was recrystallized from solvents of ethyl acetate and hexane (1:5) to give a pale yellow crystal 9.5 g (90%), mp 131–132° C., $\delta_H$(CDCl$_3$; 300 MHz): 7.59(s, 4H, Ar—H), 7.44(d, J=8.7, 2H, Ar—H), 6.82(d, J=8.7, 2H, Ar—H), 5.16(s, 1H, OH).

References

1 Shen, D., Diele, S., Pelzl, G., Wirth, I. and Tschierske, C., *J. Matter. Chem.*, 1999, 9, 661.
2 Praefcke, K., Kohne, B. and Singer, D., *Angew. Chem. Int. Ed. Engl.*, 1990, 29, 177.
3 Bouchta, A., Nguyen, H. t., Achard, M. F., et al., *Liq. Crystals*, 1992, 12, 575.
4 Hsieh, C. J. and Hsiue, G. H., *Liq. Crystals*, 1994, 16, 469.

EXAMPLE 3

Inhibiting Formation of Infectious HSV-1 Particles by Treatment with a Di-Hydroxylated Tolan Cultures of African green monkey kidney cells (Vero) cells, obtained from the American Type Culture Collection, Rockville, Md. were grown to confluence in Medium 199 supplemented with 5% fetal bovine serum, 0.075% NaHCO$_3$, and 50 μg/ml gentamycin sulfate in 25 cm$^2$ tissue culture flasks. Cells were infected with HSV-1 at a multiplicity of infection (moi) of one and incubated at room temperature for one hour to allow for virus attachment to and penetration of the cell. Under these conditions, approximately half of the cells are infected with virus. Thereafter, the cultures were rinsed three time with media and incubated in medium containing 50 μM or 75 μM 4, 4'-dihydroxytolan prepared in 0.2% dimethyl-sulfoxide (DMSO). Controls were treated identically, but were incubated without the dihyroxylated tolan. For purposes of comparison, HSV cell were also inoculated in the presence of 52.5 μM 4,4'-dihydroxystilbene. Due to the higher cell toxicity of the stilbene, cells were not incubated in the presence of 75 μM dihydroxystilbene.

Upon addition of the medium to the cultures and at 24 hours time periods thereafter, i.e., 0 hours, 24 hours, 48 hours, and 72 hours after addition of the drug, cells and medium were frozen at −70° C. Samples were then thawed, sonicated and titrated on Vero cells to determine the number of plaque forming units (pfu's) of virus produced by each culture.

Figure 4:
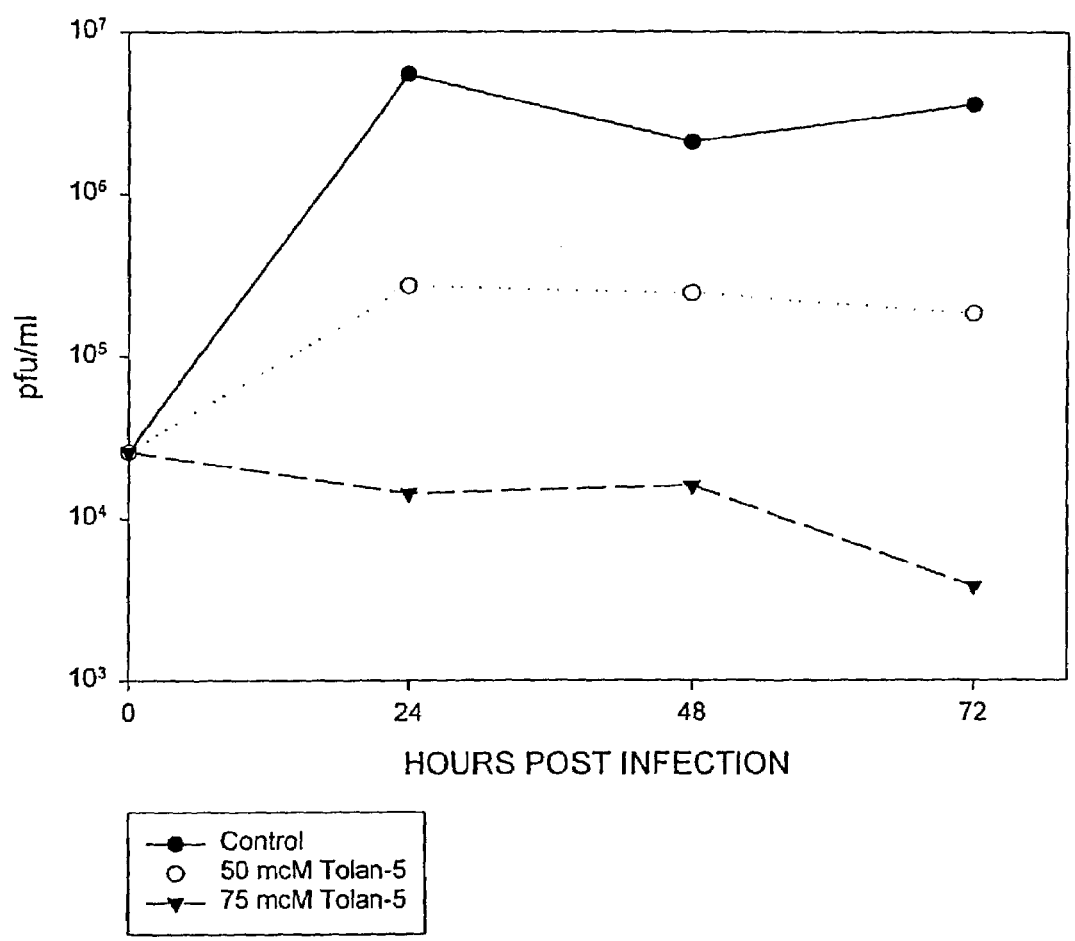
FIG. 4 is a graph showing the extent of HSV-1 replication in virus-infected cells treated with different concentrations of a dihydroxylated tolan.

As shown in FIG. 4, the number of pfu's produced in the control cultures infected with an moi of 1 reaches peak production at approximately 24 hours after infection. At this time, the system is exhausted, i.e., active virus has infected and destroyed not only those cells infected during the initial one hour of incubation but also those cells which became infected with virus released by the initially-infected cells. The lack of increase observed in the control cultures at 72 hours treatment indicates that the virus production has peaked, due to the lack of viable cells in which to reproduce.

As shown in FIG. 4, treatment of cells with 75 μM 4,4'-dihydroxytolan inhibited formation of infectious virus particles in HSV-1 infected cells by more than 99% at 24 hours. By 72 hours, infectious HSV particles were virtually undetectable in cultures continuously incubated in the presence of 75 μM 4,4'-dihydroxytolan, Treatment with 50 μM 4,4'-dihydroxytolan reduced new virus production by only 95%. In contrast, treatment of the HSV infected cells with 50 μM 4,4'-dihydroxystilbene had no effect on virus production. (data not shown) These results also demonstrate that inhibition of virus replication by the dihydroxylated tolan is dose dependent.

EXAMPLE 4

Inhibiting Formation of Infectious HSV-1 Particles by Contacting Cells with a Hydroxylated Tolan Prior to or During an Early Stage in Replication Vero cell cultures were infected with HSV-1 as described above in Example 3 except that the cells were infected with virus at an moi of 10. Under these conditions nearly all of the cells are infected with virus during the initial one hour incubation period. Following removal of unattached virus, the virally-infected cultures were incubated in control medium lacking a hydroxylated tolan or medium to which 105 μM 4,4'-dihydroxytolan had been added at 1, 3, 6, or 9 hours after removal of the unattached virus. At 24 hours after infection, the number of pfu's present in the cells and medium of untreated and hydroxylated tolan-treated cultures was determined.

Figure 5:
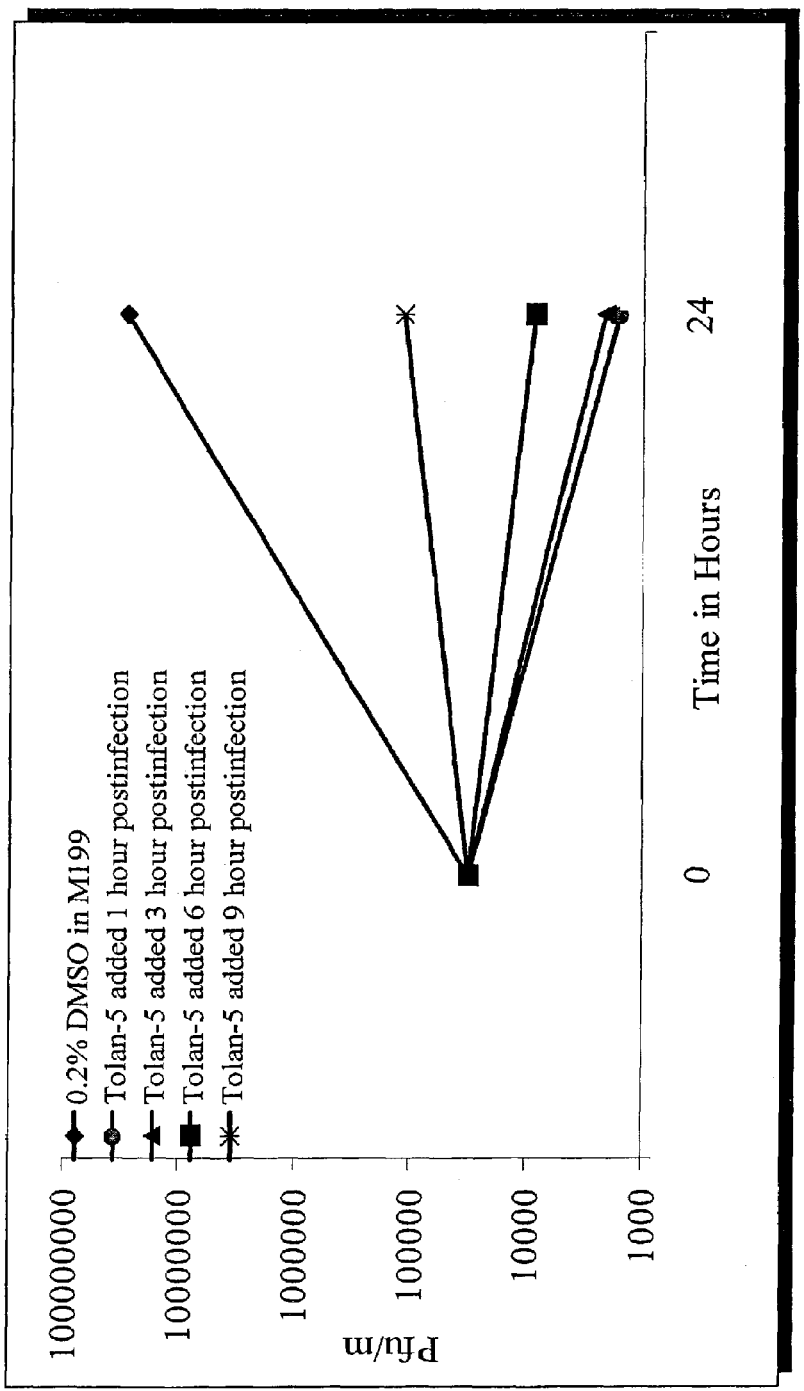
FIG. 5 is a graph showing the extent of HSV-1 replication in virus-infected cells treated with 4,4' dihydroxytolan at different times following infection.

The results presented in FIG. 5 demonstrate that the hydroxylated tolan is most effective when administered to virally-infected cells during the early stages of viral replication. In cultures treated with 105 μM 4,4'-dihydroxytolan at one hour after infection, production of virus was reduced by more than 99%. In cultures treated with 105 μM 4,4'-dihydroxytolan at 3 or 6 hours after infection, the production of virus was inhibited by approximately 90%. When the hydroxylated tolan was added 9 hours after infection, formation of infectious virus particles was not inhibited.

To determine whether hydroxylated tolans block formation of infectious herpes virus particles by directly inactivating the virus, a standard inoculum of HSV-1 was mixed with 105 μM 4,4'-dihydroxytolan in medium, with 0.2% DMSO in medium, or with media alone and placed at room temperature. The number of residual pfu's present at 1, 10, 30, and 60 minutes after addition of each respective solution to the virus was determined by plaque assay. The results demonstrated that the hydroxylated tolan did not directly inactivate HSV (data not shown).

Studies also demonstrated that the hydroxylated tolan did not prevent attachment of HSV-1 to cells. (data not shown)

EXAMPLE 5

Inhibiting HSV Replication

Vero cells were grown to confluence and infected with HSV-1 at an moi of 1 and then incubated in media lacking a hydroxylated tolan (control cultures) or in media containing 105 μM 4,4'-dihydroxytolan. One set of infected cells was maintained in the dihydroxylatedtolan for a period of 72 hours. In another set of infected cells the dihydroxytolan-containing media was replaced with media lacking a hydroxylated tolan at 24 hours. In another set of cells the tolan-containing media was replaced with media lacking the hydroxylated tolan at 48 hours after infection. The number of infectious HSV particles produced by each set of infected cells was determined by plaque assay.

Figure 6:
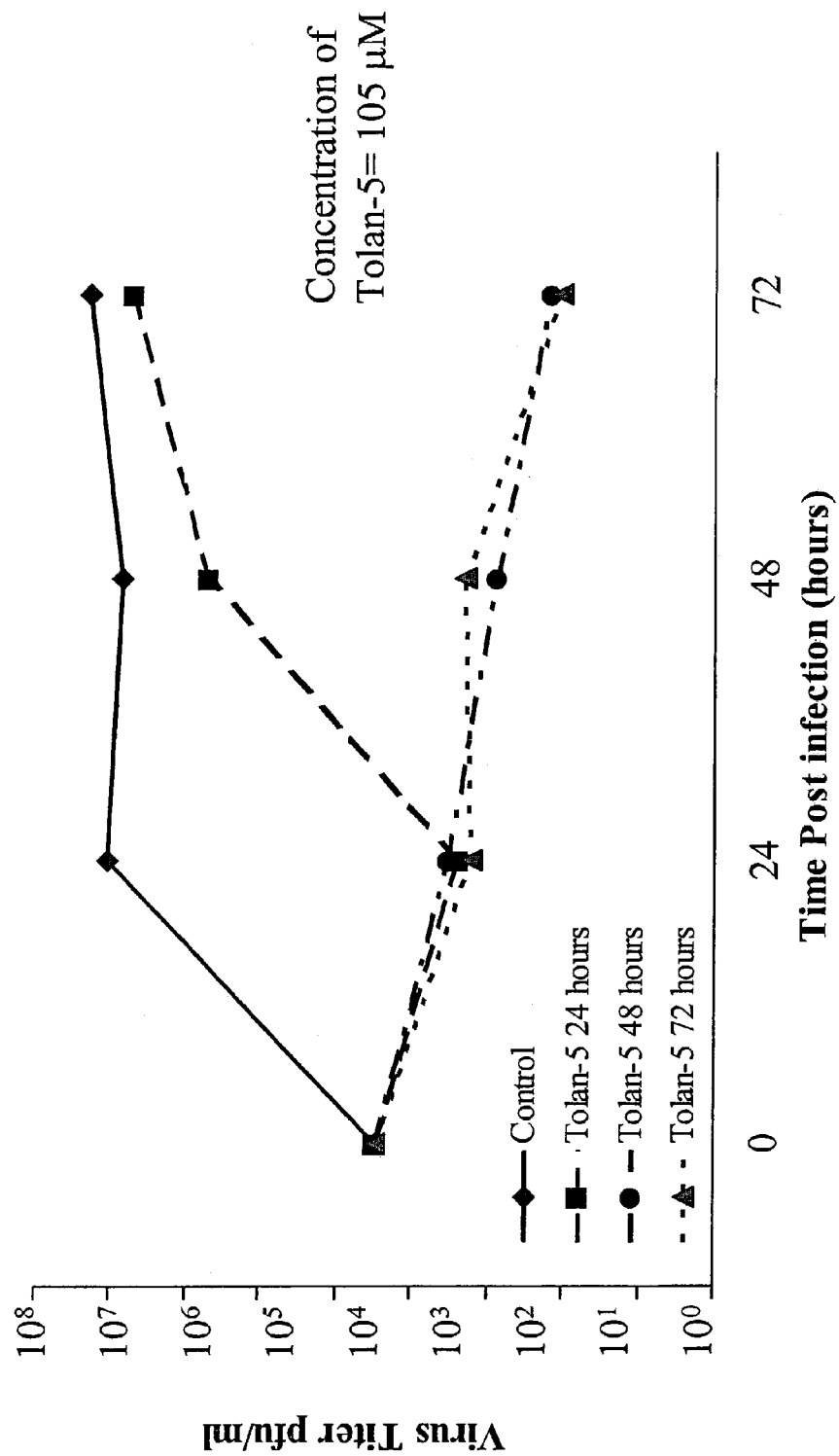
FIG. 6 is a graph depicting the reversibility of the inhibitory effect of 4,4'-dihydroxytolan on HSV-1 replication in virus-infected cells.

The results shown in FIG. 6 demonstrate that the inhibitory effect of 105 μM 4,4'-dihydroxytolan on HSV replication in virus infected cells is reversible. Accordingly, continuous treatment of HSV-infected cells with the hydroxylated tolan maintains the virus in a non-infectious state. Discontinuing treatment with the hydroxylated tolan allows replication of the virus to proceed in what appears to be a normal fashion. The results presented in FIG. 6 also suggest that HSV replication in the hydroxylated tolan treated cells was blocked at an early phase, i.e., replication of HSV had not progressed past the stage where cells are so damaged that they are unable to support replication of this herpes virus.

The results presented in FIG. 6 also indicate that exposure of mammalian cells to 105 μM 4,4'-dihydroxytolan for a prolonged period of time does not kill the cells. Cell viability studies confirmed that treatment of uninfected Vero cells with 105 μM 4,4'-dihydroxytolan for 24 hours was not toxic.

EXAMPLE 6

Characterizing Viral Proteins Produced in the Presence of a Polyhydroxylated Tolan ICP-4 and ICP-27 are immediate-early regulatory proteins of HSV-1 that are required for efficient replication of this virus. To determine whether ICP-4 or ICP-27 production is altered by treatment with a hydroxylated tolan, separate cultures of Vero cells were infected with HSV-1 at an moi of 1 and incubated in control medium or medium containing 105 μM 4,4'-dihydroxytolan for 24 hours. Infected cells were scraped from the flask, collected by centrifugation, and resuspended in cold tris-buffered saline, pelleted by centrifugation, and the cell pellet frozen at −70° C. Proteins were extracted from the thawed pellets, separated by 6–15% SDS-PAGE, and assayed on a Western blot by reacting with mouse monoclonal antibody to ICP-4 or ICP-27 from Goodwin Institute for Cancer Research Inc., FL.

Figure 7:
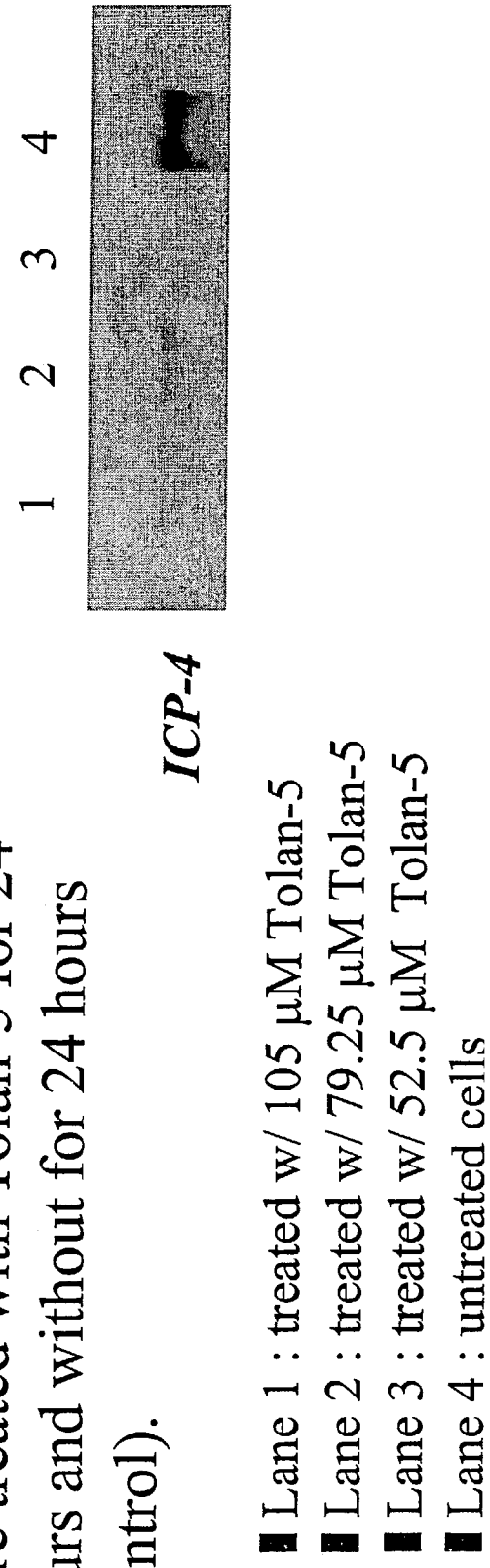
FIG. 7 is a graph depicting the effect of treatment with 4,4'-dihydroxytolan on the accumulation of ICP-4 in HSV-1 infected cells.
Figure 8:
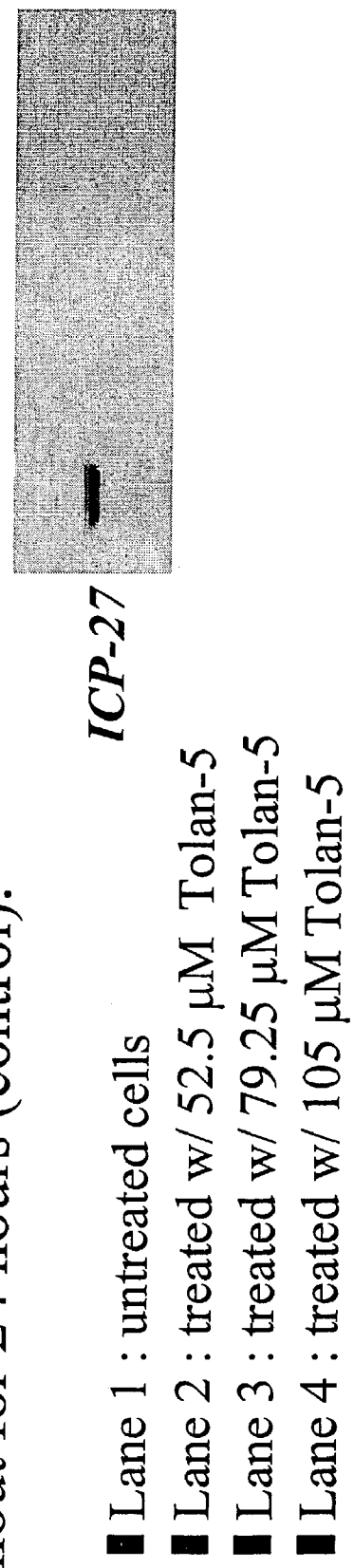
FIG. 8 is a graph depicting the effect of treatment with 4,4'-dihydroxytolan on the accumulation of ICP-27 in HSV-1 infected cells.

As shown in FIGS. 7 and 8, treatment of HSV-infected cells with the dihydroxytolan significantly reduced synthesis of ICP-4 and ICP-27, two major regulatory protein. These results confirm that treatment with a hydroxylated-tolan inhibits synthesis of herpes viruses at an early phase in the replicative scheme. These results also indicate that cultured cells treated with a hydroxylated tolan are a useful model system for characterizing the herpes virus gene products that are made during the immediate early phase and early phase of HSV replication.

EXAMPLE 8

Cell Toxicity of Tolans

Cell toxicity of the tolans 4,4'-dihydroxytolan ("Tolan-5"), 3,4',5-trihydroxytolan ("Tolan-10") and 4-hydroxy-4'-trifluoromethyltolan ("Tolan-11") was determined using an MTT assay. In this assay, cells are exposed to MTT, 3-(4,5-dimethylthiazol-2-yl)-2,5-diphenyltetrazolium bromide, which is taken into the cells and reduced by mitochondrial dehydrogenase to a purple formazan, a large molecule which is unable to pass through intact cell membranes, and therefore accumulates in healthy cells. The ability of cells to reduce MTT is an indication of mitochondrial integrity and activity, which may be interpreted as a measure of viability. Solubilization of the cells results in the liberation of the product which can readily be detected spectrophotometrically.

Various concentrations of Tolan-5, Tolan-10 and Tolan-11 were added to 96 well tissue culture plates that had been seeded with Vero cells. The plates were then incubated at 37° C. in 5% $CO_2$/95% air for 24, 48 and 72 hours. At the end of each time point, 50 μl of MTT (1 mg/ml) was added to the tissue culture plates which were then incubated for an additional four hours. At the end of that time, dimethyl sulfoxide (DMSO) was added to dissolve the cells and formazan, and the plates were read spectrophotometrically at 540 nm. From this data a $CD_{50}$ or the concentration of the respective tolan required to render 50% of the cells non-viable was calculated. Presented in Table I below are the toxicity results for Tolan-5, Tolan-10, and Tolan-11 measured at 24, 48 and 72 hours of treatment.

TABLE 1

$CD_{50}$ for hydroxylated Tolans of Examples 1 and 2:
Toxicity was measured using a MTT colorimetric assay
at 48 hours in Vero cells, and reported as the
cytotoxic dose ($CD_{50}$ in μM, based on a
50% reduction in cell viability.

| | $CD_{50}$ in μM | | |
|---|---|---|---|
| | Time in hours | | |
| Name | 24 | 48 | 72 |
| Tolan - 5 | — | 106 | 84.0 |
| Tolan - 10 | >200 | >200 | >200 |
| Tolan - 11 | 72.1 | 48.2 | 47.1 |

As shown in Table 1, Tolan-10 showed very little toxicity. The estimated $CD_{50}$ for this trihydoxytolan is >200 μm. The hydroxytrfluoromethyltolan, Tolan-11, was more toxic than the other hydroxylated tolans and is, thus, less preferred.

EXAMPLE 9

Inhibition of HSV-1 Replication In Vitro

Tissue culture cells were infected with HSV-1 and incubated in solutions containing Tolan-5, Tolan-10 and Tolan-11. The concentrations used ranged from one-half to three-quarters of the calculated $CD_{50}$ for the respective tolan at 48 hours of treatment.

Specifically, Vero cells were infected with HSV-1 at a multiplicity of infection of one for one hour. At the end of that time, the cultures were rinsed with media and fresh media containing various concentration of the respective tolan were added. Infected control cultures were incubated in media lacking hydroxylated tolan. At 1, 24, 48, and 72 hours after infection, samples were frozen at −70° C. until assayed for new virus production. Virus production was quantified by the plaque assay for each time point of infection. The results, which are expressed as plaque forming units per milliliter (pfu/ml).

Figure 9:
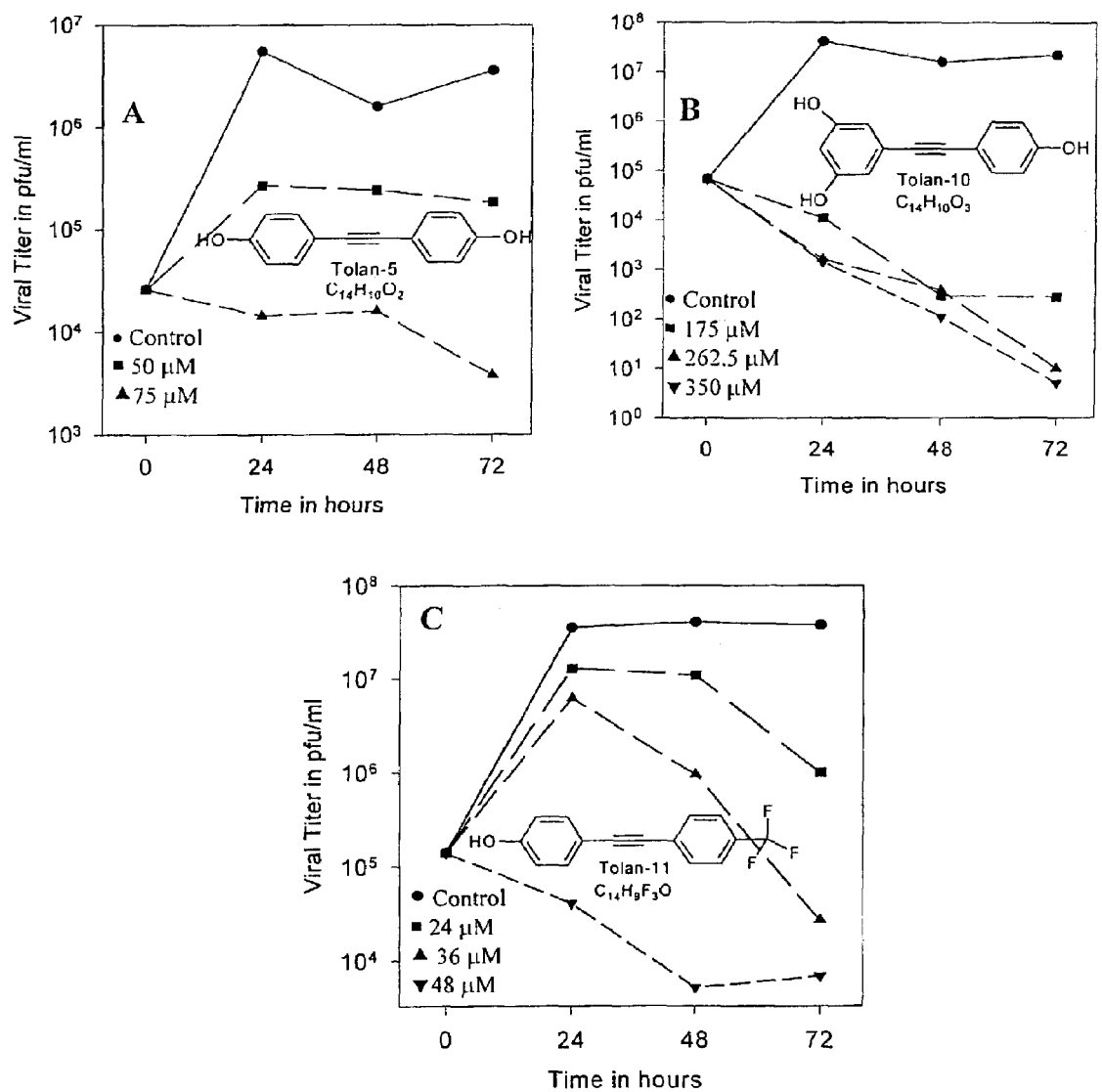
FIGS. 9A, 9B, and 9C are graphs showing the inhibitory effects of 4,4' dihydroxytolan ("Tolan-5"), 3,4',5-trihydroxytolan ("Tolan-10") and 4-hydroxy-4'-trifluoromethyltolan ("Tolan-11"), respectively, on replication of HSV-1 in infected cells.

As shown in FIGS. 9A–C, Tolan-5, Tolan-10, and Tolan-11 all inhibited HSV-1 production, but to varying degrees. Tolan-5 (FIG. 9A) was more inhibitory to the virus at 75 μm that at 50 μm. Tolan-10 (FIG. 9B) was equally effective against the virus at all concentrations, which ranged from a high of 350 μm to a low of 175 μm. Tolan-11 had little to no effect at concentration of less than 48 μm.

When inhibition occurred, it was seen with all tolans at the earliest time point assayed, which was 24 hours after cell infection. Once suppressed, the virus did not recover over the 72 hour time period the cells were tested for virus production.

EXAMPLE 10

Inhibition of HSV In Vivo

Female SKH-1 hairless mice 4–5 weeks old were lightly anesthetized and a scratch approximately 2–3 mm long and 0.25 mm deep was made on the lateral dorsal aspect of the neck. The scratch was infected with $10^6$ plaque forming units of HSV-1. One hour later, the infected scratch area was treated with a 5% or 10% solution of Tolan-10 in DMSO. This treatment was repeated three times a day for five days. There were at least six mice in each treatment group. Untreated mice and mice treated with DMSO only were used as controls.

Beginning on day 1 and continuing for 10–11 days, the scratch site was examined daily for evidence of an HSV infection and scored according to the following schedule:
0=no visible change on skin by scratch
1+=papules around scratch
2+=papules around scratch ulcerate with scab formation
3+=ulcerative zosterform spread along peripheral nerves to flank of animal
4+=ulcerative lesions open on flank
5+=death/sacrifice The data was grouped according to treatment and statistically analyzed for significance.

Figure 10:
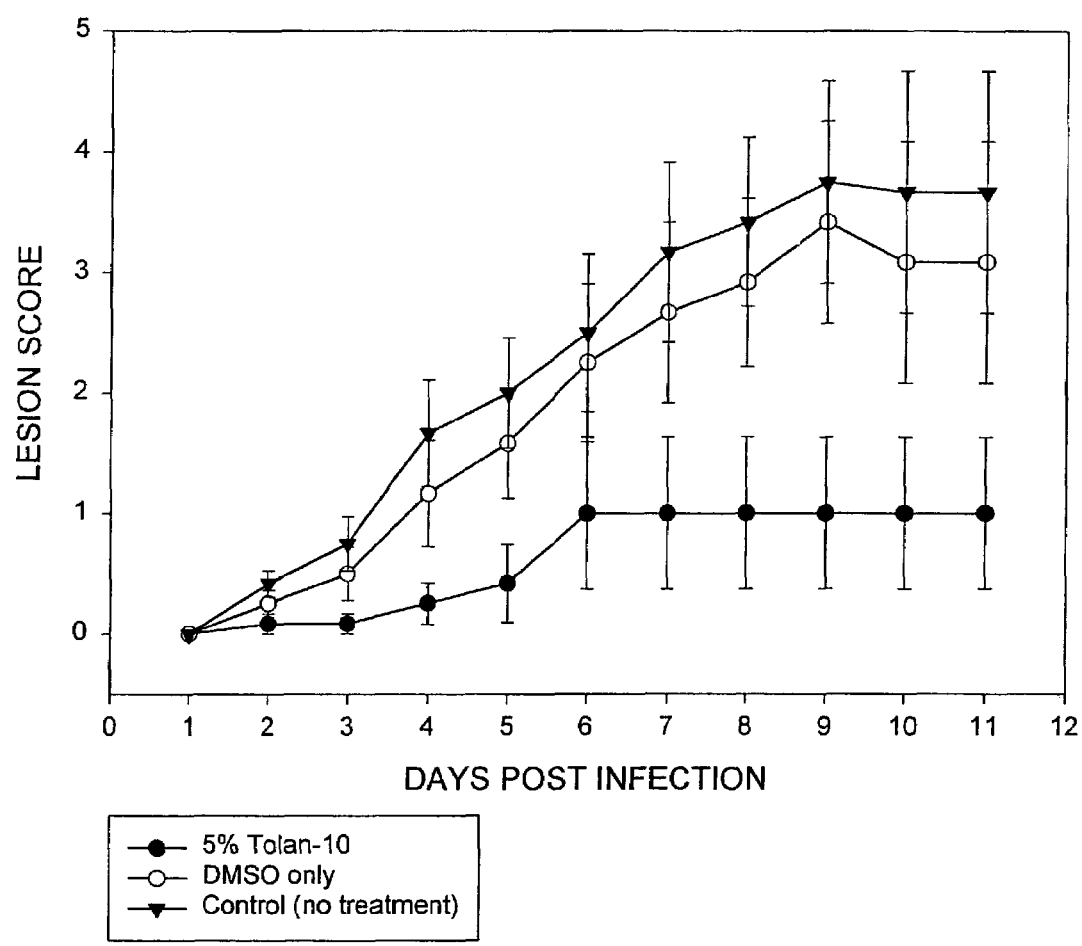
FIG. 10 is a graph showing the effect of a 5% Tolan-10 solution on the development of herpetic lesions in animals infected with HSV-1.
Figure 11:
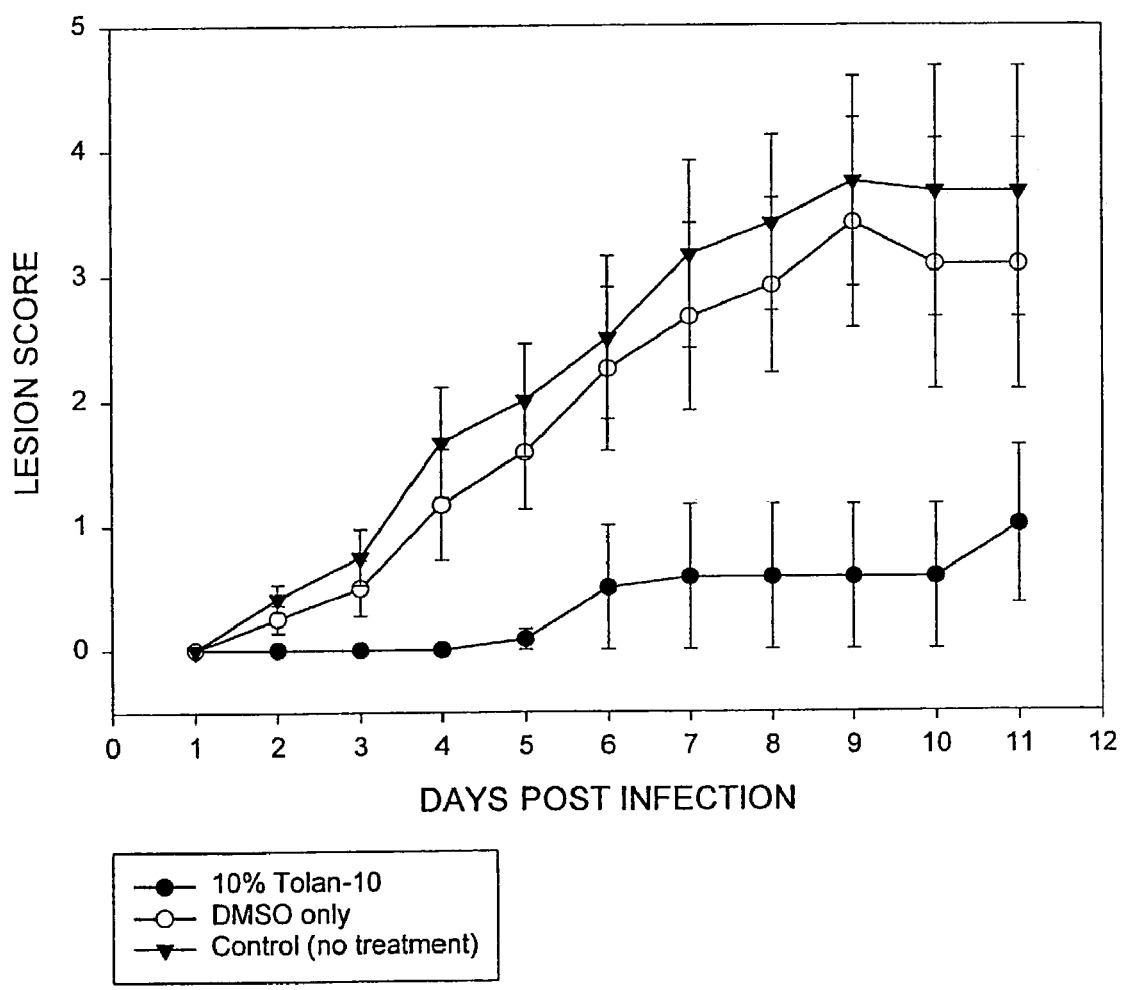
FIG. 11 is a graph showing the effect of a 10% Tolan-10 solution on the development of herpetic lesions in animals infected with HSV-1.
Figure 12:
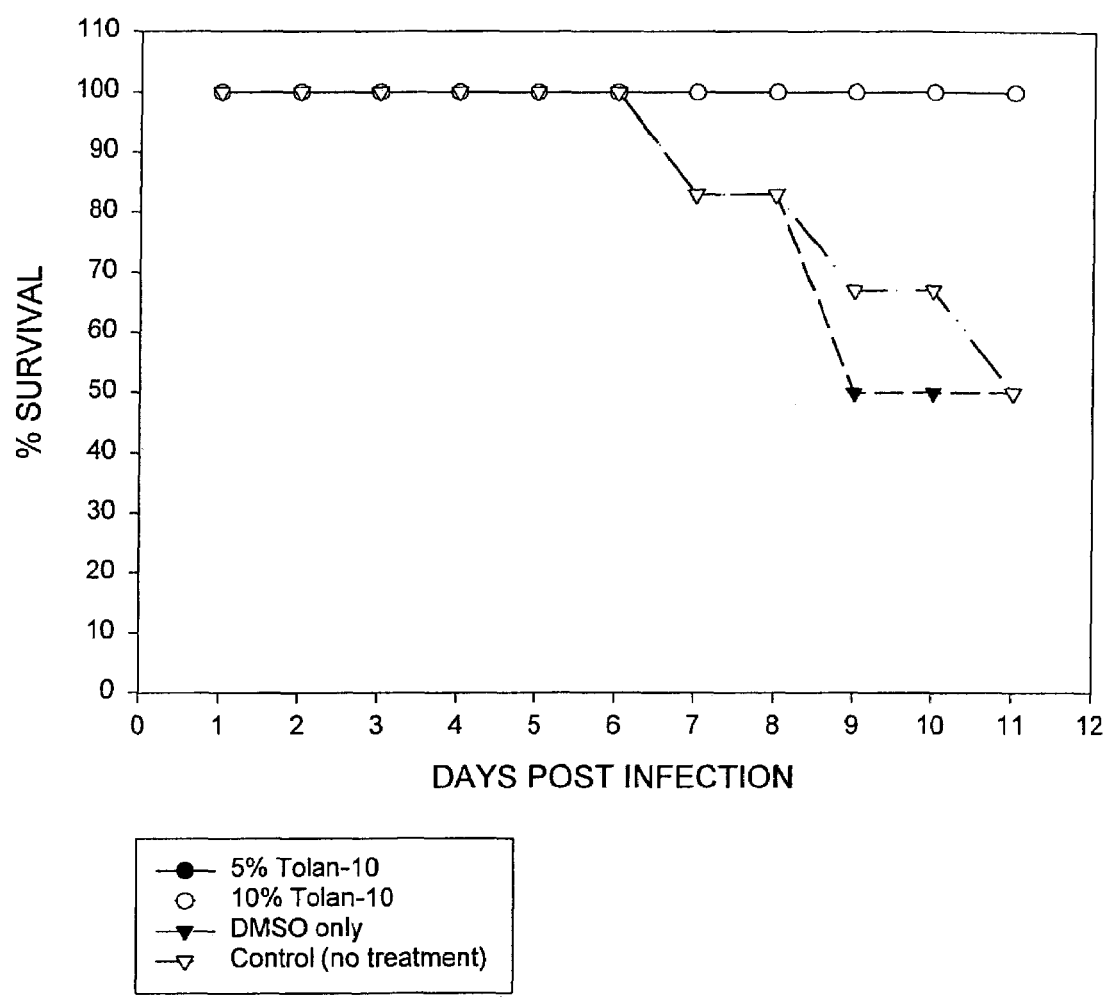
FIG. 12 is a graph showing the percentage of control animals and tolan-treated animals that survive an infection with HSV-1.

As shown in FIGS. 10 and 11, Tolan-10 at concentrations of 5 and 10% significantly reduced the severity of HSV lesions when compared to untreated controls or animals that were treated with DMSO only. This difference was evident as early as three days after infection. Although not significantly different, 10% Tolan-10 appeared to be slightly more effective than 5% Tolan-10, particularly on days 6–10. At day 11, however, there was no difference between the two treatment groups.

Survival data is shown in FIG. 11. While 50% of the animals in the DMSO control and no treatment control groups died within 11 days after infection, none of the animals treated with 5% or 10% tolan perished during this time period.

EXAMPLE 11

Inhibiting Growth of Neisseria gonorrhea by Treatment with Tolan-10

Various concentrations of the trihydroxytolan Tolan-10 were incorporated into chocolate agar plates that were prepared using standard procedures. The trihydroxylated tolan was first dissolved in DMSO and medium and then added to liquid chocolate agar, which was then poured into petri plates and allowed to solidify. The highest concentration of DMSO in the agar was 0.5%. Control plates containing chocolate agar and DMSO at a final concentration of 0.5% were also prepared.

Neisseria gonorrhea CDC 98 was obtained from Difco Laboratories. The authenticity of the bacterium was confirmed utilizing standard microbiological techniques of identification. Cultures of the bacterial isolate were inoculated onto fresh plates of solidified chocolate agar and then 24 hours later, a suspension was made from isolated colonies.

10 μl aliquots of the suspension were spread evenly across the surface of solidified control chocolate agar lacking tolan and the surface of solidified chocolate agar containing Tolan-10 at final concentrations ranging from 1 to 125 μg/ml. Thereafter, the agar plates were incubated at 37° C. with or without 5% $CO_2$. All plates were visually examined for growth of the bacterium 24 hours later to determine the concentration of the tri-hydroxylated tolan that inhibits growth by 50% ($MIC_{50}$) as well as the concentration which inhibits any visible growth ($MIC_{100}$).

The effect of the same concentrations of Tolan-10 on the growth of Escherichia coli, Staphylococcus aureus, Streptococcus pyogenes, Pseudomonas aeruginosa, Neisseria meningitidis and Candida albicans was also determined. As shown in Table II below, Tolan 10 selectively inhibited Neisseria gonorrhoeae. The $IC_{50}$ value of the tri-hydroxylated tolan for this bacterium at 24 hours of treatment was 50 μg/ml and the $IC_{100}$ value was 100 μg/ml. In contrast, Tolan 10, at the highest concentration tested, had no effect on the other microorganisms listed.

TABLE 2

| IC's of Tolan - 10 against bacteria and C. albicans | | |
| --- | --- | --- |
| Microorganism | $IC_{50}$ (mg/L) | $IC_{100}$ (mg/L) |
| N. gonorrhoeae | 50 | 100 |
| N. meningitides | >125 | >125 |
| E. coli | >125 | >125 |
| S. aureus | >125 | >125 |
| S. pyogenes | >125 | >125 |
| P. aeruginosa | >125 | >125 |
| C. albicans | >125 | >125 |

What is claimed is:

1. A method of treating gonorrhea caused by Neisseria gonorrhea, comprising administering a composition comprising a trihydroxylated tolan to a subject in need thereof, wherein the composition is administered to the subject in an amount effective to inhibit growth of Neisseria gonorrhea.

2. The method of claim 1, wherein the pharmaceutical composition is administered to the eye, oropharynx, genitalia, or rectum of the subject.

3. The method of claim 1, wherein the trihydroxylated tolan is 3,4',5-trihydroxytolan.

* * * * *